United States Patent
Ayinde et al.

(10) Patent No.: US 12,213,840 B2
(45) Date of Patent: Feb. 4, 2025

(54) AUTOMATICALLY ESTABLISHING MEASUREMENT LOCATION CONTROLS FOR DOPPLER ULTRASOUND

(71) Applicant: EchoNous, Inc., Redmond, WA (US)

(72) Inventors: Babajide Ayinde, Redmond, WA (US); Matthew Cook, Redmond, WA (US); Eric Wong, Redmond, WA (US); Alexandra Clements, Redmond, WA (US); Dave Willis, Redmond, WA (US); Pavlos Moustakidis, Redmond, WA (US); Vasileios Sachpekidis, Redmond, WA (US); Niko Pagoulatos, Redmond, WA (US)

(73) Assignee: EchoNous, Inc., Redmond, WA (US)

( * ) Notice: Subject to any disclaimer, the term of this patent is extended or adjusted under 35 U.S.C. 154(b) by 4 days.

(21) Appl. No.: 17/693,848

(22) Filed: Mar. 14, 2022

(65) Prior Publication Data
US 2023/0285005 A1    Sep. 14, 2023

(51) Int. Cl.
*A61B 8/00* (2006.01)
*A61B 8/06* (2006.01)
*A61B 8/08* (2006.01)

(52) U.S. Cl.
CPC ............ *A61B 8/54* (2013.01); *A61B 8/06* (2013.01); *A61B 8/085* (2013.01); *A61B 8/0883* (2013.01);
(Continued)

(58) Field of Classification Search
CPC .. A61B 8/54; A61B 8/06; A61B 8/085; A61B 8/0883; A61B 8/463; A61B 8/469; A61B 8/488
See application file for complete search history.

(56) References Cited

U.S. PATENT DOCUMENTS 10,430,946 B1    10/2019    Zhou et al.
10,631,828 B1    4/2020    Hare, II et al.
(Continued)

FOREIGN PATENT DOCUMENTS

EP            3536245 A1    9/2019
WO    WO 2018026431 A1    2/2018
(Continued)

OTHER PUBLICATIONS

American Institute of Ultrasound in Medicine, "AIUM Practice Guideline for the Performance of the Focused Assessment With Sonography for Trauma (FAST) Examination," *J Ultrasound Med* 33:2047-2056, 2014.
(Continued)

*Primary Examiner* — Baisakhi Roy
*Assistant Examiner* — Kaitlyn E Sebastian
(74) *Attorney, Agent, or Firm* — Seed Intellectual Property Law Group LLP

(57) ABSTRACT

A facility for automatically establishing measurement location controls for Doppler ultrasound studies is described. The facility receives a first ultrasound image, and user input selecting an anatomical structure appearing in it. The facility performs localization to determine the location of the selected anatomical structure in the initial image, and determines a first placement of measurement location controls relative to the structure. On the ultrasound machine, the facility invokes one or more first Doppler ultrasound modes using the first placement. The facility receives a second ultrasound image produced by the ultrasound machine using the one or more first modes; determines a flow location and direction based on the second ultrasound image; and determines a second placement relative to the flow location. The facility invokes one or more second Doppler ultrasound modes using the second placement, and receives results
(Continued)

from the invocation of the one or more second Doppler ultrasound modes.

14 Claims, 16 Drawing Sheets
(13 of 16 Drawing Sheet(s) Filed in Color)

(52) U.S. Cl.
CPC .............. *A61B 8/463* (2013.01); *A61B 8/469* (2013.01); *A61B 8/488* (2013.01)

(56) References Cited

U.S. PATENT DOCUMENTS

| | | | | |
|---|---|---|---|---|
| 2014/0018680 | A1* | 1/2014 | Guracar | A61B 8/5276 600/440 |
| 2014/0098049 | A1* | 4/2014 | Koch | A61B 8/461 345/173 |
| 2017/0360403 | A1* | 12/2017 | Rothberg | A61B 8/02 |
| 2018/0259608 | A1 | 9/2018 | Golden et al. | |
| 2019/0140596 | A1 | 5/2019 | Shimamoto et al. | |
| 2020/0054306 | A1 | 2/2020 | Mehanian et al. | |
| 2020/0155124 | A1* | 5/2020 | Halmann | A61B 8/5276 |
| 2020/0260062 | A1 | 8/2020 | Sharma et al. | |
| 2021/0022716 | A1* | 1/2021 | Kerby | A61B 8/469 |
| 2021/0345992 | A1 | 11/2021 | Cook et al. | |
| 2021/0350529 | A1 | 11/2021 | Ayinde et al. | |

FOREIGN PATENT DOCUMENTS

| | | |
|---|---|---|
| WO | WO 2018140596 A2 | 8/2018 |
| WO | WO 2019201726 A1 | 10/2019 |
| WO | WO 2020020809 A1 | 1/2020 |

OTHER PUBLICATIONS

Gal, Y., et al., "Dropout as a Bayesian Approximation: Representing Model Uncertainty in Deep Learning," Proceedings of the 33rd International Conference on Machine Learning, New York, NY, 2016, retrieved from arXiv:1506.02142v6, 12 pages.
Geifman, Y., et al., "Selective Classification for Deep Neural Networks," Jun. 2, 2017, retrieved from arXiv:1705.08500v2, 12 pages.
International Search Report and Written Opinion, mailed Aug. 25, 2021, for International Application No. PCT/US2021/031415, 10 pages.
International Search Report and Written Opinion, mailed Feb. 24, 2022, for International Application No. PCT/US2021/058037. (11 pages).
International Search Report and Written Opinion, mailed Oct. 12, 2021, for International Application No. PCT/US2021/031193, 9 pages.
Lakshminarayanan, B., et al., "Simple and Scalable Predictive Uncertainty Estimation Using Deep Ensembles," 31st Conference on Neural Information Processing Systems (NIPS 2017), Long Beach, CA, retrieved from arXiv:1612.01474v3, 15 pages.
Liu, S. et al., "Deep learning in Medical Ultrasound Analysis: A Review," (2019). Engineering, 5(2): 261-275.
Redmon et al., "YOLOv3: An Incremental Improvement," Apr. 8, 2018, retrieved from arxiv.org/abs/1804.02767, 6 pages.

\* cited by examiner

U.S. 12,213,840 B2

AUTOMATICALLY ESTABLISHING MEASUREMENT LOCATION CONTROLS FOR DOPPLER ULTRASOUND

BACKGROUND

Ultrasound imaging is a useful medical imaging modality. For example, internal structures of a patient's body may be imaged before, during or after a therapeutic intervention. Also, qualitative and quantitative observations in an ultrasound image can be a basis for diagnosis. For example, ventricular volume determined via ultrasound is a basis for diagnosing, for example, ventricular systolic dysfunction and diastolic heart failure.

A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired presentation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

Spectral analysis is often performed to assess blood flow direction and measure velocity for cardiac valves, vascular and other pathological lesions (a region in an organ or tissue which has suffered damage through injury or disease). Spectral analysis can be performed using either continuous wave (CW) or pulsed wave (PW) Doppler. CW uses two crystals to continuously transmit and receive signal. It is generally used to measure high blood flow velocities, such as above 2 m/sec. PW, on the other hand, uses a single crystal to transmit and wait to receive and analyze the returning signal. PW is typically limited to measuring low blood velocities, such as below 2 m/sec, because it is subject to signal aliasing at higher blood velocities. The type of spectral analysis—CW or PW—to deploy and structures to be examined are generally determined by the suspected pathology. Sometimes color Doppler is used in conjunction with either PW or CW for more accurate gate/focal point placement.

As a basis for measuring blood flow velocity using spectral analysis, an ultrasound operator defines a region of the ultrasound cone in which measurement should be performed, using measurement location controls that vary between Doppler modes. For CW, the operator specifies a Doppler line containing the origin at the top of the ultrasound cone and a point at the curved base of the cone, and the largest velocity at any point on the line is determined. For PW, the operator specifies both a Doppler line, and a segment of that line defined by placing a gate to bound it, and the velocity along that segment of the line is determined. For color Doppler, the operator specifies a color box bounding a sample volume that is in a range of depths across a contiguous sequence of scan lines, to display flow velocity and direction in that sample volume using color. The best location to place these Doppler measurement location controls can vary depending on the structure under scrutiny, suspected pathology, and cardiac view.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
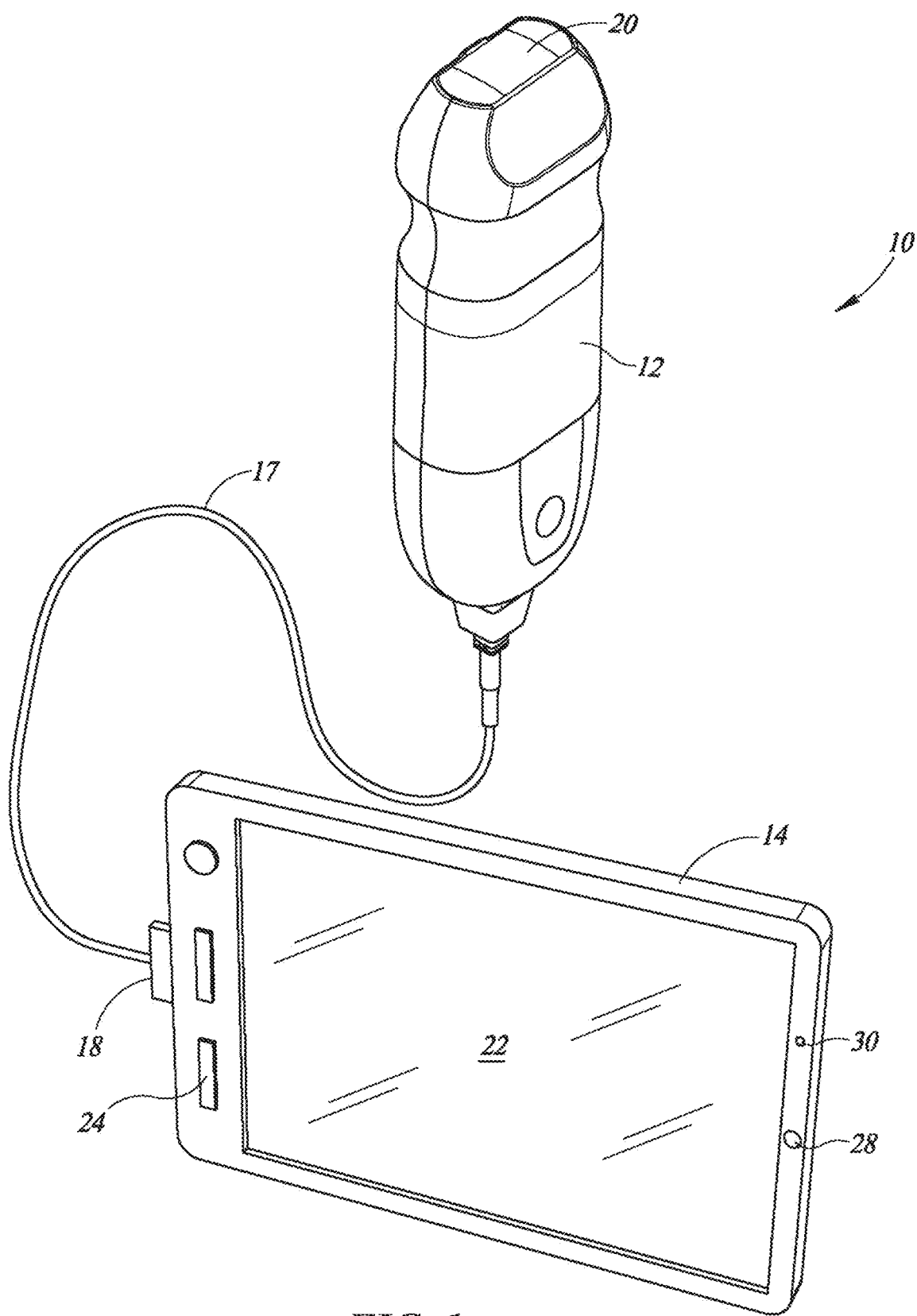
FIG. 1 is a block diagram showing some of the components typically incorporated in at least some of the computer systems and other devices on which the facility operates.

The inventors have recognized that conventional approaches to using spectral and color Doppler ultrasound have significant disadvantages.

In particular, the inventors have recognized that conventional Doppler ultrasound techniques rely on manual placement of measurement location controls, such as Doppler lines, gates, focal points, and color Doppler color boxes. This requires significant skill and experience on the part of the operator, and thus excludes operators lacking such skill and experience from performing such studies. Further, even skilled, experienced operators can consume considerable time—both of the patient and the ultrasound machine—and produce sub-optimal results.

In response to recognizing these disadvantages, the inventors have conceived and reduced to practice a software and/or hardware facility that automatically establishes measurement location controls for Doppler ultrasound studies ("the facility").

In some embodiments, the facility receives user input identifying a structure—such as a valve—with respect to which the measurement location controls are to be placed. In various embodiments, the facility receives such user input via voice, touching a display on which the ultrasound visual output is displayed at a point where the identified structure is displayed, etc.

In some embodiments, the facility performs localization to determine the location of one or more structures of interest in ultrasound images, such as cardiac valves including the mitral valve, the tricuspid valve, and the aortic valve. In various embodiments, the facility performs localization via (1) object detection to identify a region of the image containing a structure, or (2) object segmentation to identify each pixel of the image that shows the structure.

In some embodiments, the facility determines a placement of ultrasound measurement location controls relative to the location determined for the structure identified by the user, such as in the center of a valve identified by the user, or the center of a superior, interior, anterior, posterior, lateral, medial, upstream, or downstream end of the valve.

In some embodiments, the facility detects the location and/or direction of flow, such as laminar blood flow in healthy patients, and aliasing in pathological patients. In various moments, the facility performs segmentation, object detection, or linear regression to detect flow location.

In some embodiments, the facility uses the detected flow location to adjust the placement of ultrasound measurement location controls to more accurately capture the detected flow for measurement via Doppler. In some embodiments, this involves dropping the Doppler line to pass through the center of the detected flow location, and placing the gate or focal point to encompass the detected flow location.

In some embodiments, the facility compares the determined direction of flow to the direction of the Doppler line to determine whether these lines are close to parallel. If the angle between these lines is greater than the threshold, the facility takes action, such as directing the operator to reposition the probe to better align the Doppler line with the laminar flow or aliasing. In some embodiments, the facility applies trigonometry to adjust a velocity determined along the Doppler line to reflect velocity along the direction of flow.

By performing in some or all of these ways, the facility reduces the levels of operator skill and experience, time, and inaccuracy incurred by Doppler ultrasound studies.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by reducing the amount of time for which the ultrasound machine is used for a particular study, the ultrasound machine can be used for a great number of studies during its lifetime, or a version that can be used for the same number of studies can be manufactured at lower cost. Also, by reducing the number of unsuccessful studies that must be repeated, the facility increases the availability of ultrasound machines for additional original studies.

FIG. 1 is a schematic illustration of a physiological sensing device, in accordance with one or more embodiments of the present disclosure. The device 10 includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from an operator that touches the screen. In such embodiments, the user interface 24 may include a portion or the entire display screen 22, which is capable of receiving operator input via touch. In some embodiments, the user interface 24 may include one or more buttons, knobs, switches, and the like, capable of receiving input from an operator of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by an operator to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
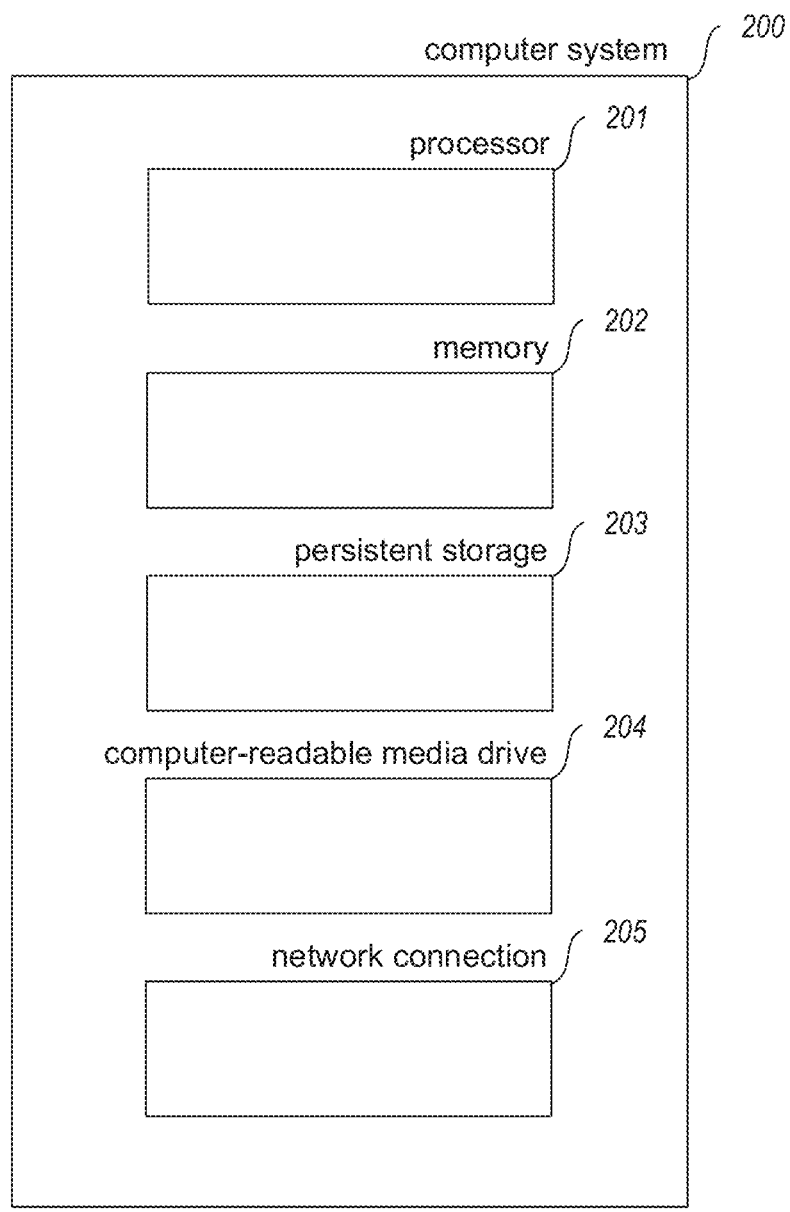
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a central processing unit (CPU), graphics processing unit (GPU), tensor processing unit (TPU), neural network processor (NNP), field-programmable gate array (FPGA), or application-specific integrated circuit; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 3:
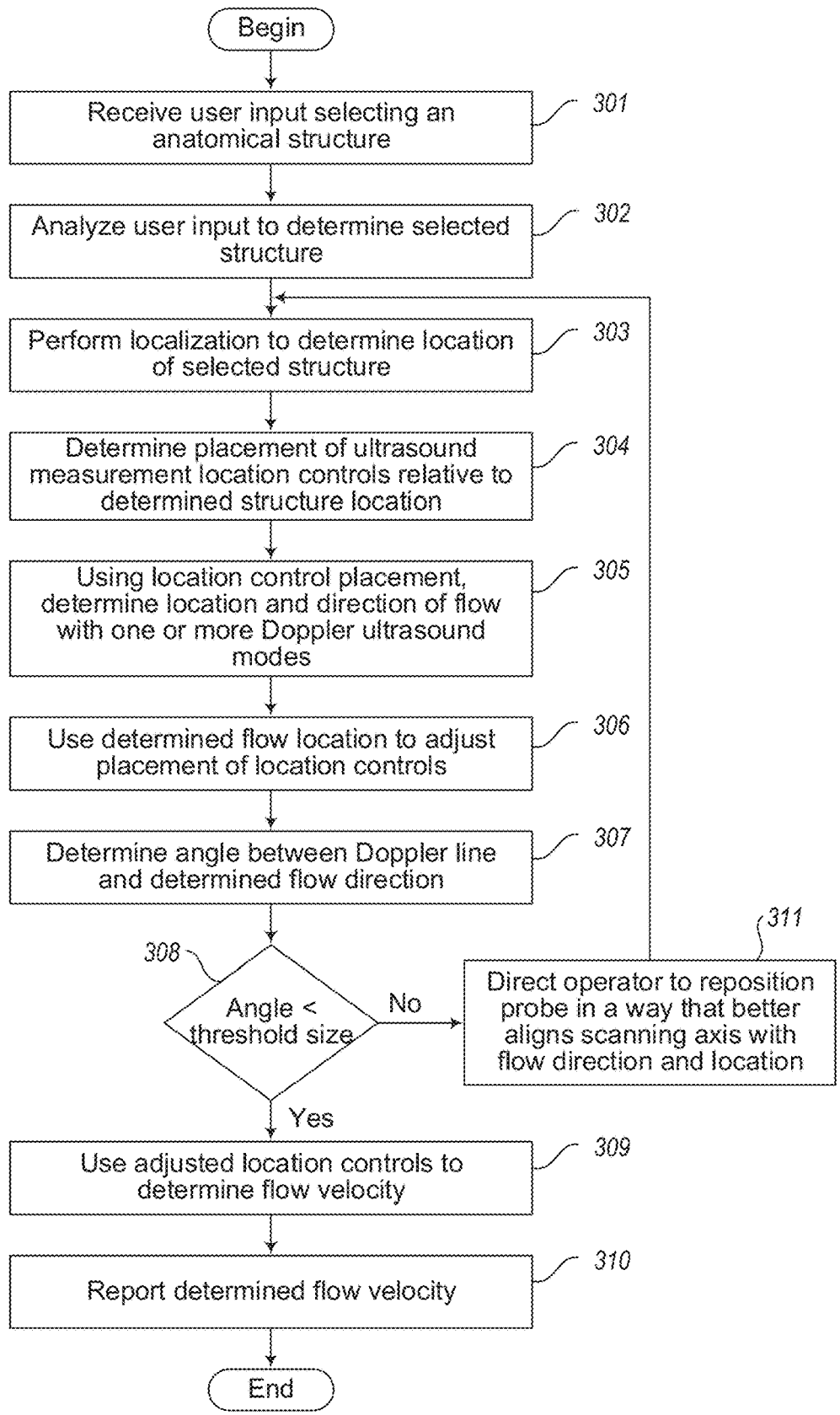
FIG. 3 is a flow diagram showing a process performed by the facility in some embodiments to automatically establish measurement location controls for Doppler ultrasound.

FIG. 3 is a flow diagram showing a process performed by the facility in some embodiments to automatically establish measurement location controls for Doppler ultrasound. In act 301, the facility receives user input selecting an anatomical structure, which can include an anatomical structure shown in an ultrasound image captured and displayed for a person. In various embodiments, the user input received by the facility in act 301 represents the operator speaking the name of the structure, or touching a particular point in the displayed ultrasound image.

Figure 4:
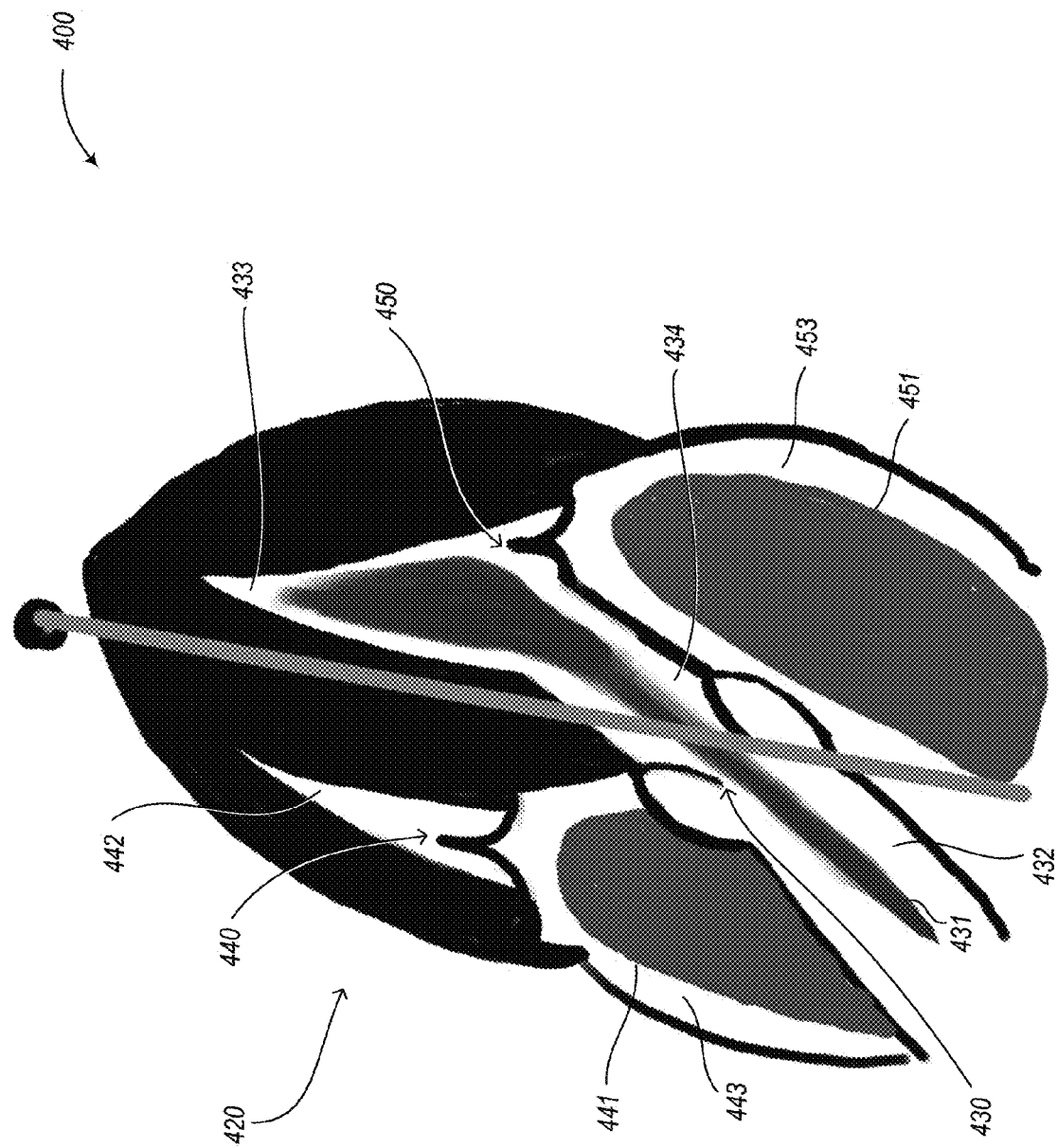
FIG. 4 is an ultrasound diagram showing a cardiac ultrasound image captured for a person.

FIG. 4 is an ultrasound diagram showing a cardiac ultrasound image captured for a person. The image 400 shows an Apical 5 chamber view of the person's heart 420. While many ultrasound images show the outline of an ultrasound cone surrounding the ultrasound image, ultrasound image 400 shown in FIG. 4 and certain of the other ultrasound images shown in the figures do not. Some of the ultrasound images shown in the figures are the subject of black/white inversion from their typical appearance to make them more visually intelligible.

In the heart, the ultrasound image shows aortic valve 430, through which blood normally flows from the left ventricle 433, through the left ventricle outflow track 434, and into the aorta 432. Using color Doppler, blue region 431 shows blood flow in that direction throughout region 431 during the ventricular systole phase of the cardiac cycle. In the figures, a blue color shows flow away from the ultrasound origin (i.e., generally downward in the drawing), and a red color shows flow toward the ultrasound origin (i.e., generally upward in the drawing). Also shown is tricuspid valve 440, through which blood normally flows from the right atrium 443 into the right ventricle 442. Red region 441 shows blood in the right atrium that is flowing upward toward the tricuspid valve. Further shown is mitral valve 450, through which blood normally flows from the left atrium 453 to the left ventricle 433. Red region 451 shows blood in the left atrium that is flowing upward toward the mitral valve. As examples, to select an anatomical structure in this ultrasound image, the operator may say the name of the mitral, tricuspid, or aortic valve, or touch the screen where one of these valves is displayed.

Returning to FIG. 3, in act 302, the facility analyzes the user input received in act 301 to determine the anatomical structure selected by the user input. In act 303, the facility performs localization to determine the location of the selected structure in an ultrasound image captured from the person. In various embodiments, the facility performs localization using object detection to identify a region of the image that contains the structure, or object segmentation to identify each of the pixels of the image that show the structure. In various embodiments, the facility performs object detection and/or segmentation in manners described in one or more of the following, each of which is hereby incorporated by reference: U.S. patent application Ser. No. 17/088,390, entitled "GATING MACHINE LEARNING PREDICTIONS ON MEDICAL ULTRASOUND IMAGES VIA RISK AND UNCERTAINTY QUANTIFICATION," filed Nov. 3, 2020; U.S. patent application Ser. No. 16/913,322, entitled "AUTOMATICALLY IDENTIFYING ANATOMICAL STRUCTURES IN MEDICAL IMAGES IN A MANNER THAT IS SENSITIVE TO THE PARTICULAR VIEW IN WHICH EACH IMAGE IS CAPTURED," filed Jun. 16, 2020; U.S. patent application Ser. No. 17/068,143, entitled "AUTOMATIC EVALUATION OF ULTRASOUND PROTOCOL TREES," filed Oct. 12, 2020; U.S. patent application Ser. No. 17/091,263, entitled "ROBUST SEGMENTATION THROUGH HIGH-LEVEL IMAGE UNDERSTANDING," filed Nov. 6, 2020; U.S. patent application Ser. No. 17/509,987, entitled "AUTOMATIC DEPTH SELECTION FOR ULTRASOUND IMAGING," filed Oct. 25, 2021; U.S. patent application Ser. No. 17/529,565, entitled "AUTOMATICALLY DETECTING AND QUANTIFYING ANATOMICAL STRUCTURES IN AN ULTRASOUND IMAGE USING A CUSTOMIZED SHAPE PRIOR," filed Nov. 18, 2021; U.S. patent application Ser. No. 17/678,813, entitled "DETERMINING HEART RATE BASED ON A SEQUENCE OF ULTRASOUND IMAGES," filed Feb. 23, 2022. In cases where a document incorporated herein by reference conflicts with the present disclosure, the present disclosure controls.

In act 304, the facility determines a placement of ultrasound measurement location controls relative to the structure location determined in act 301. As examples: for color Doppler, the facility determines the location for a color box; for CW, the facility determines location for a Doppler line; for PW, the facility determines the location of a Doppler line and a segment of that line bounded by a gate. In various embodiments, the placement determined by the facility is in the center of a valve selected by the user, or in the center of an end of the valve, such a superior, inferior, anterior, posterior, lateral, medial, normally-upstream, or normally-downstream end of the valve.

Figure 5:
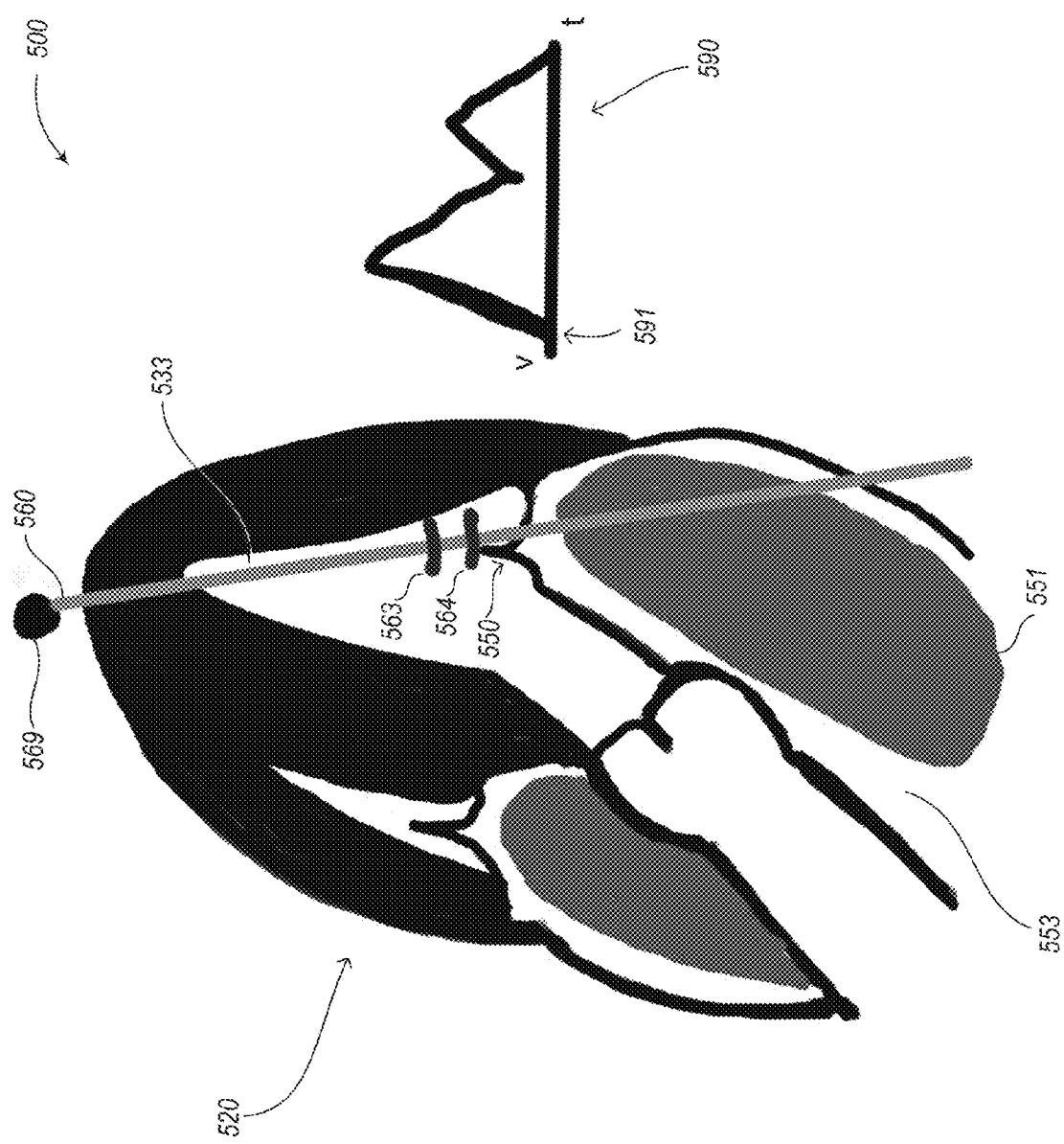
FIG. 5 is an ultrasound diagram showing a first time at the beginning of the diastole phase.

FIGS. 5-9 are a series of sample ultrasound diagram showing an example of the facility's placement of measurement location controls over the course of a ventricular diastole phase of the cardiac cycle in a healthy heart. FIG. 5 is an ultrasound diagram showing a first time at the beginning of the diastole phase. The diagram 500 shows a heart 520 in which the facility has placed measurement location controls by (1) dropping a Doppler line 560 from the origin 569 at the top of the diagram through the center of mitral valve 550, and (2) establishing walls 563 and 564 of a Doppler gate at points along the length of the Doppler line that surround a space immediately on the normally-downstream side of the mitral valve. Placed in this way, the ultrasound in one or more Doppler modes will measure the velocity of blood along the Doppler line between these two walls. In a properly-functioning heart, the direction of flow will be from the left atrium 553 to the left ventricle 533 over the course of the subsequent portion of the ventricular diastole phase. At this point, however, with the mitral valve closed, the facility measures the velocity of blood within the gate near zero, though red region 551 shows that blood is flowing toward the closed mitral valve in the left atrium. Velocity versus time graph 590 shows this measured zero velocity at the time 591 to which the diagram 500 corresponds.

Figure 6:
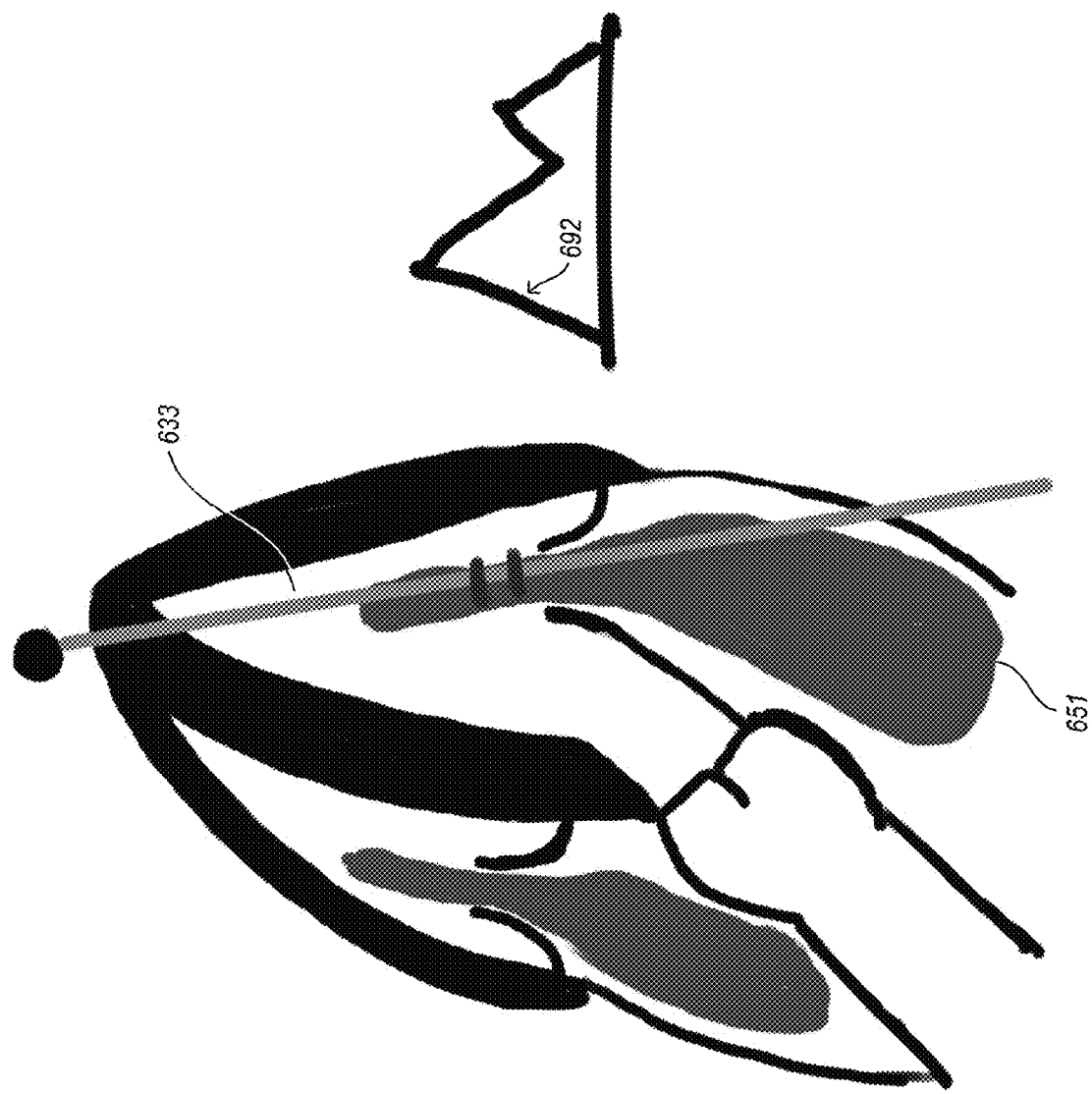
FIG. 6 is an ultrasound diagram showing a second time in the diastole phase.

FIG. 6 is an ultrasound diagram showing a second time in the diastole phase. At the second time, shown as time 692 on the velocity graph, diastole phase is proceeding, and the velocity along the Doppler line within the gate is climbing. This can be seen mirrored in the expansion of red region 651 into the left ventricle 633, as compared with red region 551 shown in FIG. 5.

Figure 7:
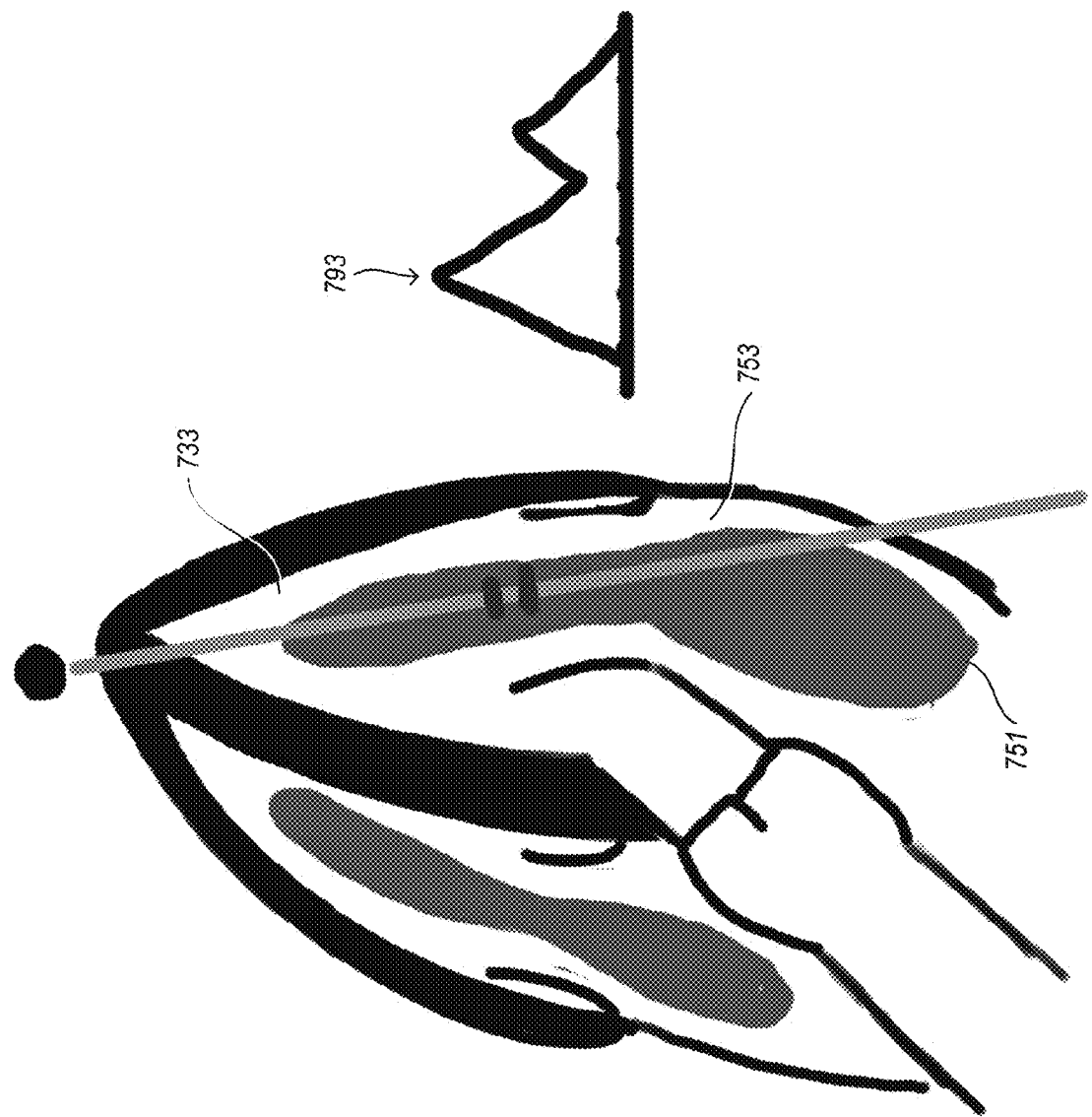
FIG. 7 is an ultrasound diagram showing a third time in the diastole phase.

FIG. 7 is an ultrasound diagram showing a third time in the diastole phase. At the third time, shown as time 793 on the velocity graph, diastole phase is proceeding further, and the velocity along the Doppler line within the gate is at its maximum. This corresponds to red region 751 shifting further from the left atrium 753 to the left ventricle 733, as compared with red region 651 shown in FIG. 6.

Figure 8:
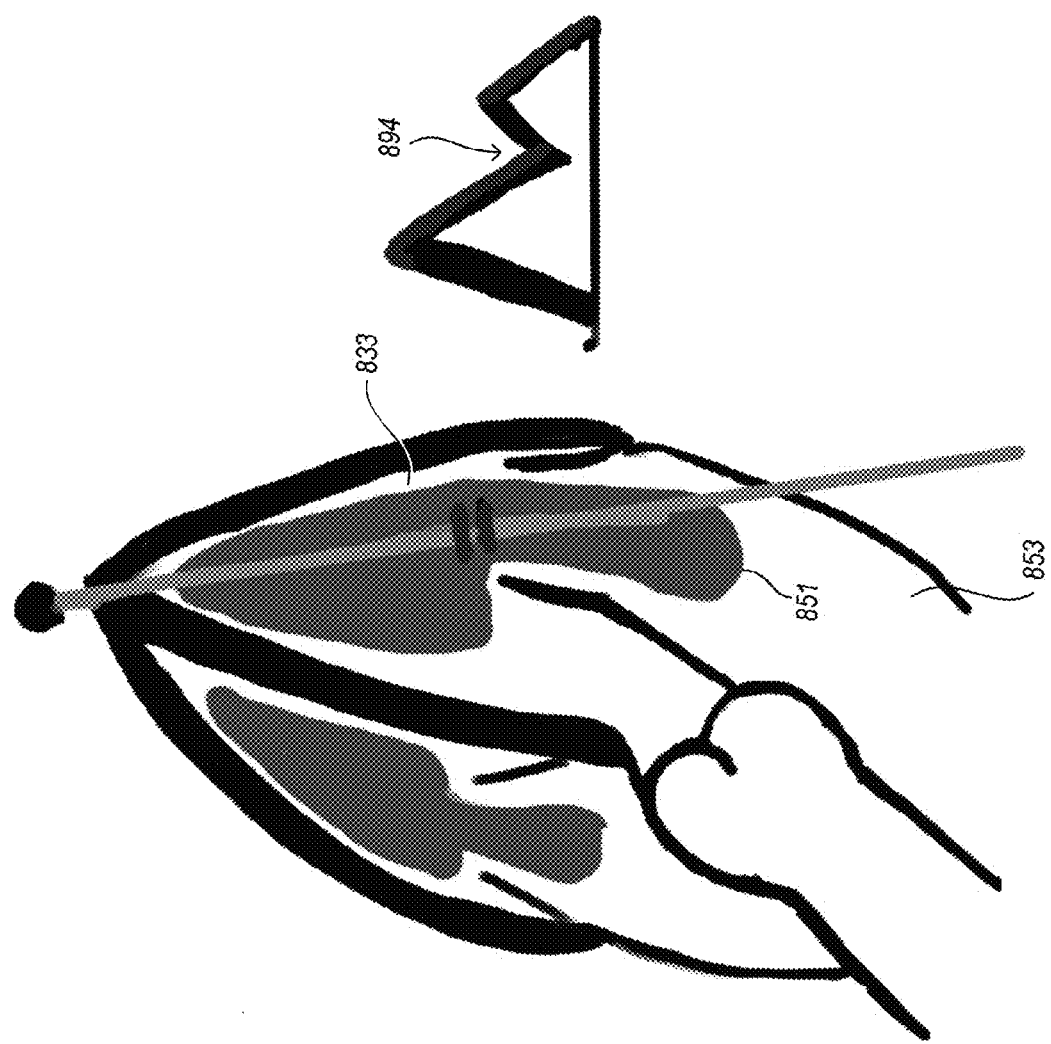
FIG. 8 is an ultrasound diagram showing a fourth time in the diastole phase.

FIG. 8 is an ultrasound diagram showing a fourth time in the diastole phase. The fourth time, shown as time 894 on the velocity graph, is at or near the diastasis stage of the diastole phase, at which the velocity through the mitral valve and placed gate is at its minimum during diastole. This is reflected in red region 851 shifting yet further from the left atrium 853 to the left ventricle 833.

Figure 9:
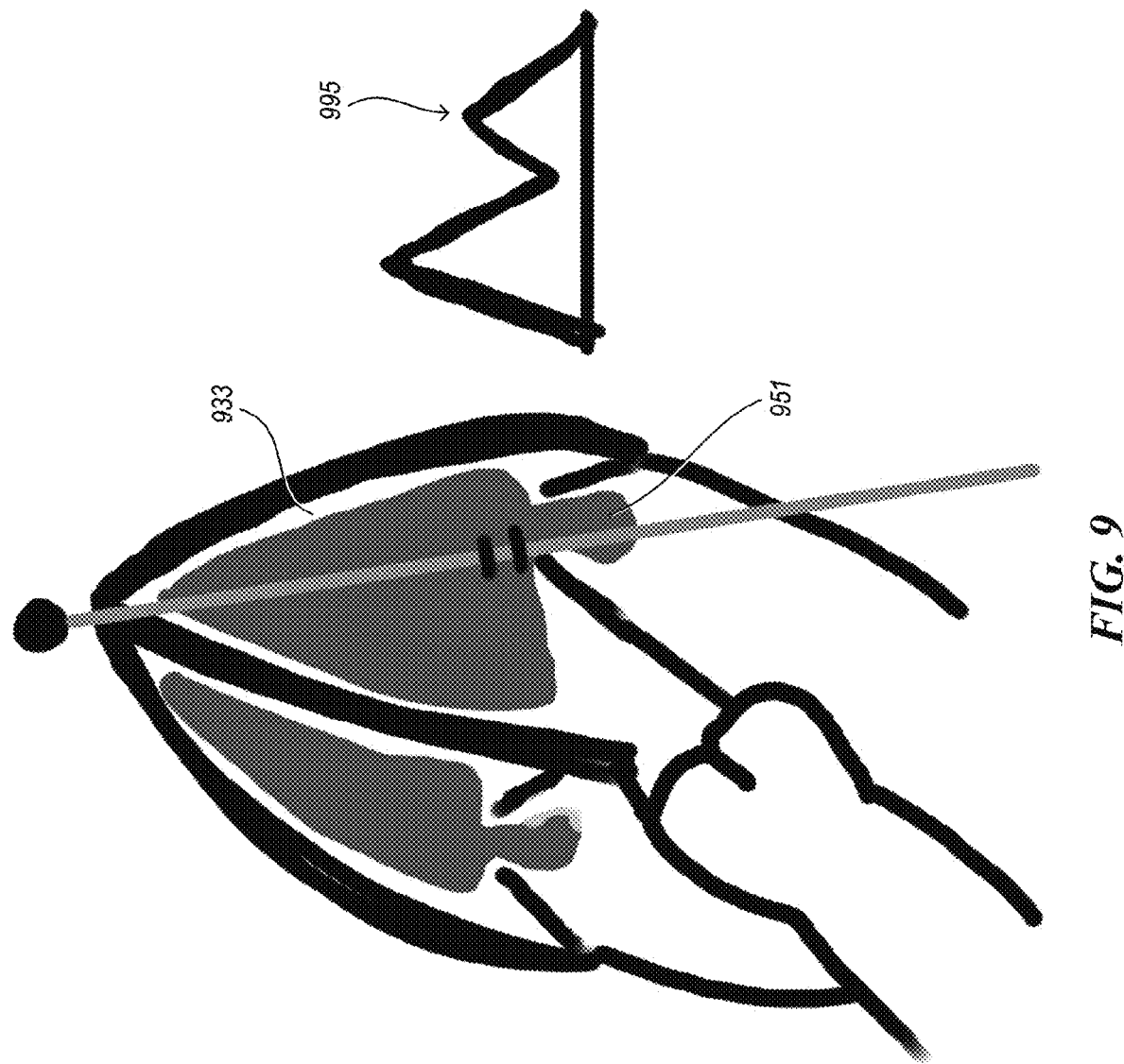
FIG. 9 is an ultrasound diagram showing a fifth time in the diastole phase.

FIG. 9 is an ultrasound diagram showing a fifth time in the diastole phase. The fifth time, shown as time 995 on the velocity graph, corresponds to a second, lower peak in velocity, reflected in most of the red region 951 being within the left ventricle 933.

Returning to FIG. 3, in act 305, the facility uses the location control placement determined in act 304 to determine a location and direction of flow using one or more Doppler ultrasound modes. In various embodiments, the facility determines the location and direction of flow using object detection or object segmentation against Doppler ultrasound images produced using the location control placement. In some cases, the flow of interest is normal, laminar blood flow through the heart. In some cases, the flow of interest is regurgitation, which can constitute backflow relative to the proper flow of blood through the heart, and/or turbulent flow; in such cases, in some embodiments, the facility performs localization with respect to aliasing patterns in ultrasound image that represent this aberrant blood flow.

In various embodiments, the facility determines the location and direction of flow using segmentation, object detection, or linear regression. For the segmentation approach, in some embodiments the facility trains and applies a convolutional neural network whose independent variables are color Doppler and B-mode images, and whose dependent variable is a probability map signifying the spatial location of aliasing in the image and the direction of the flow. For the object detection approach, in some embodiments the facility parameterizes the output bounding box by height, width, and angle of rotation. For the linear regression approach, in some embodiments the facility parameterizes by two points that go through the center of laminar flow or aliasing.

In act 306, the facility uses the flow location determined in act 305 to adjust placement of the location controls. In some embodiments, the facility performs this adjustment by dropping the Doppler line to pass through the center of the detected flow location, and placing the gate or focal point along that Doppler line to encompass the detected flow location.

Figure 10:
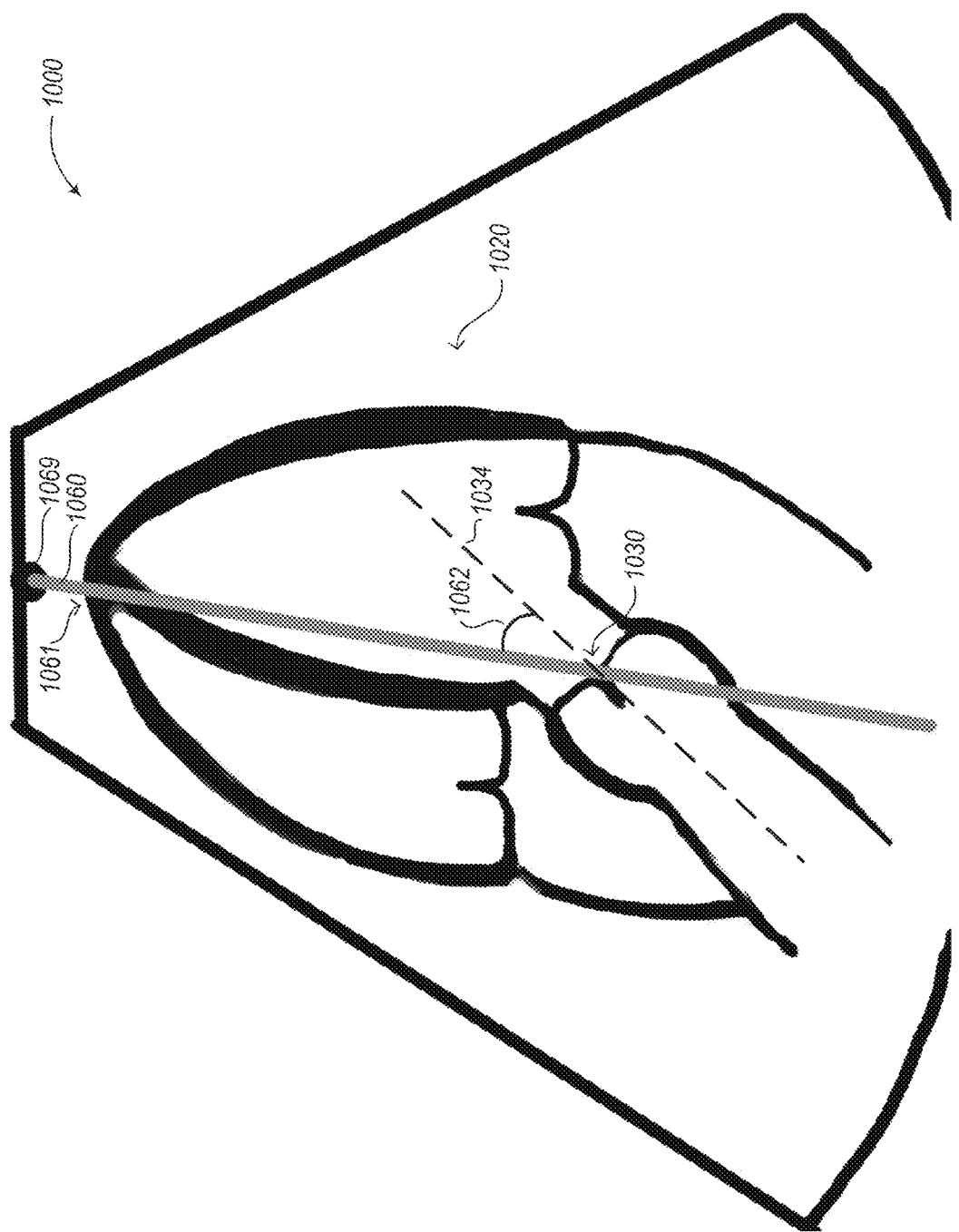
FIG. 10 is an ultrasound diagram showing an example of determining the angle between a Doppler line and a determined flow direction.

In act 307, the facility determines the angle between the Doppler line and the flow direction determined in act 305. FIG. 10 is an ultrasound diagram showing an example of determining the angle between a Doppler line and a determined flow direction. It can be seen in the diagram 1000 that the Doppler line 1060 begins at the origin 1069 at the top of the diagram; intersects the exterior wall of the heart 1020 at point 1061; and passes through the center of aortic valve 1030. The determined direction of flow is shown as broken line 1034. The facility determines angle 1062 between the Doppler line and the direction of flow.

Returning to FIG. 3, in act 308, if the size of the angle determined in act 307 is less than a threshold angle size, such as 10°, then the facility continues in act 309, else the facility continues in act 311. In act 309, the facility uses the location controls as adjusted in act 306 to determine flow velocity. In act 310, the facility reports the determined flow velocity. In various embodiments (not shown), the facility makes a variety of uses of the determined flow velocity, such as displaying it, storing it on behalf of the person, using as a basis for making other ultrasound observations, making automatic diagnoses, etc. As one example, stenosis can be automatically diagnosed based upon high blood flow velocity in the normal direction. After act 310, this process concludes. In act 311, because the size of the angle exceeded the threshold size, the facility declines to use the present location control placement to determine flow velocity, and instead directs the operator of the ultrasound machine to reposition its probe in a way that better aligns the scanning axis of the probe with the direction and location determined for the flow in act 305. This can involve, for example, swiveling, fanning, and/or relocating the probe with respect to the outside of the person's body. In various embodiments, the facility performs this direction via synthesized or recorded speech output; overlaying text on the ultrasound display; overlaying pictorial animation on the ultrasound display; displaying text and/or pictorial animation on a separate visual display; etc. After act 311, the facility continues in act 303 to use localization to determine the location of the selected structure in the new ultrasound view resulting from repositioning of the probe.

Those skilled in the art will appreciate that the acts shown in FIG. 3 may be altered in a variety of ways. For example, the order of the acts may be rearranged; some acts may be performed in parallel; shown acts may be omitted, or other acts may be included; a shown act may be divided into subacts, or multiple shown acts may be combined into a single act; etc.

Figure 11:
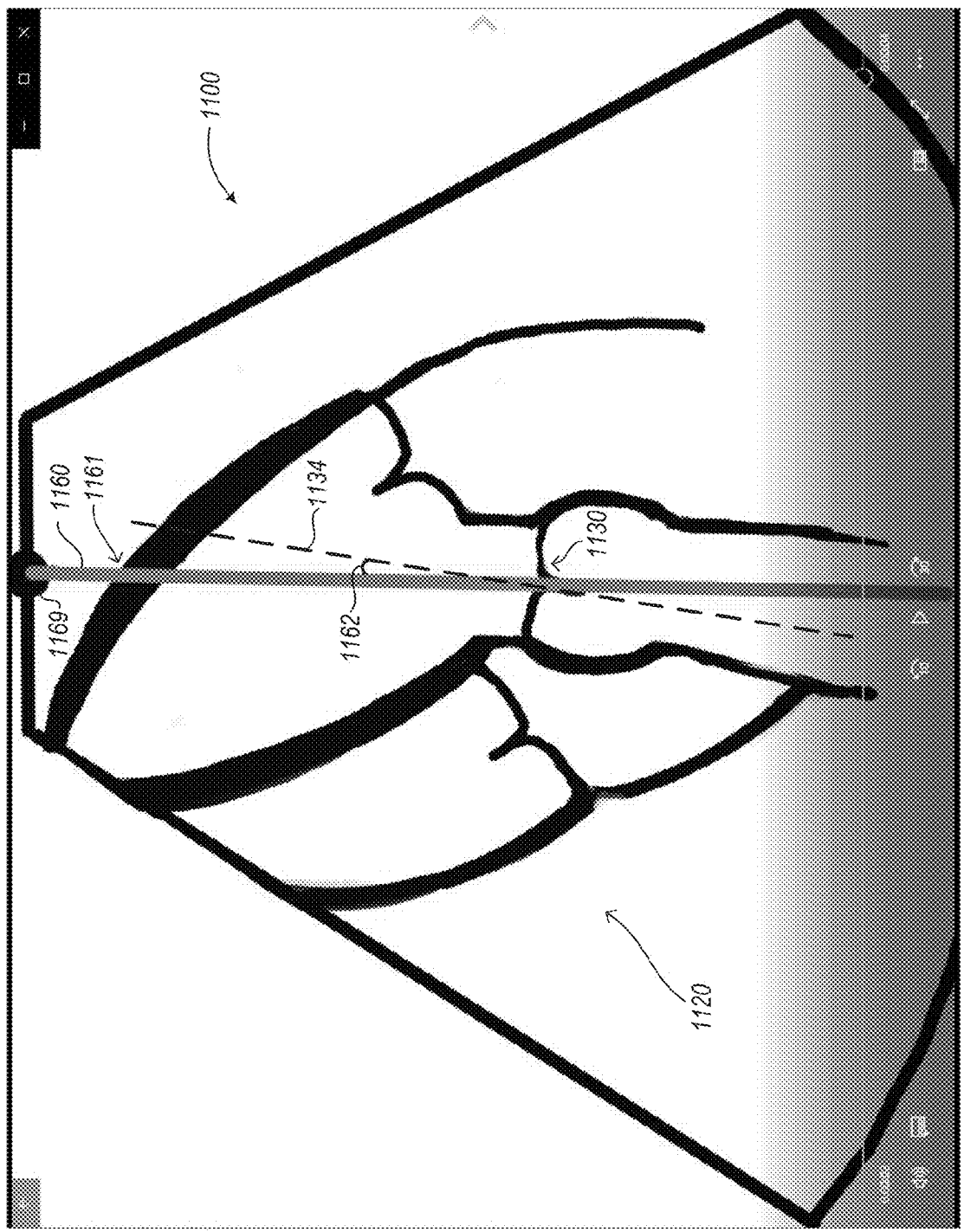
FIG. 11 is a sample ultrasound diagram showing repositioning of the ultrasound probe in a way that better aligns the scanning axis with the direction location determined by the facility for flow.

FIG. 11 is a sample ultrasound diagram showing repositioning of the ultrasound probe in a way that better aligns the scanning axis with the direction location determined by the facility for flow. After the repositioning, the facility establishes Doppler line 1160 beginning at the origin 1169 at the top of diagram 1100, intersecting the exterior wall of the heart 1120 at point 1161, and passing through the center of aortic valve 1130. Line 1134 shows the direction determined for the flow by the facility. Angle 1162 between these two lines is significantly lesser than angle 1062 shown in FIG. 10. Accordingly, Doppler line 1160 is better aligned with the flow direction, and the component of flow velocity measured along the Doppler line is much closer to the flow velocity in the flow direction. Accordingly, in this repositioned orientation, in some cases the velocity measured along the Doppler line can be used as a reasonable proxy for velocity in the direction of flow. In some embodiments, the facility adapts the velocity measured along the Doppler line by dividing it by the cosine of the angle to estimate velocity along the direction of flow.

Figure 12:
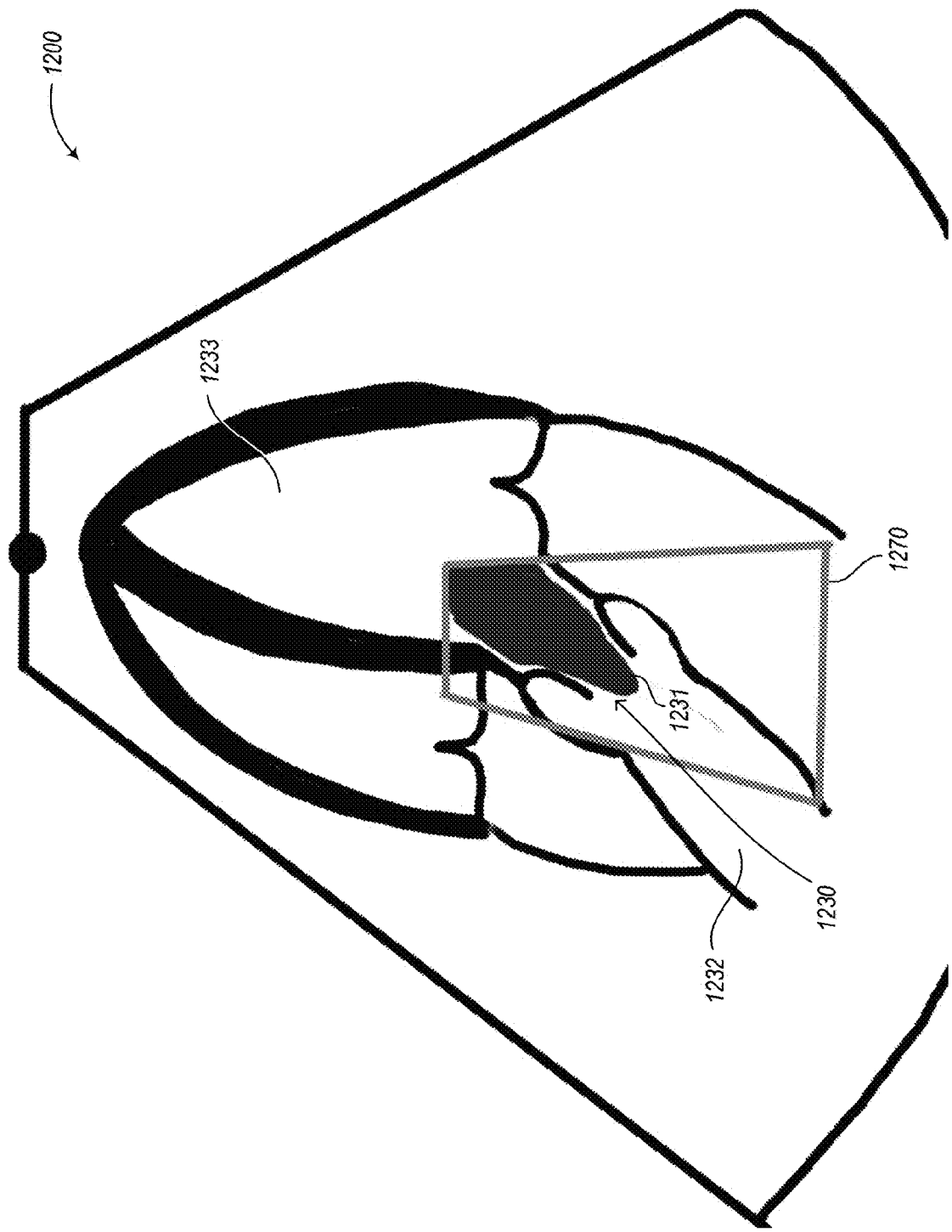
FIG. 12 is a sample ultrasound diagram showing the pathological heart at a first time.

FIGS. 12-16 are a series of sample ultrasound diagrams captured during the systole phase of the cardiac cycle showing an example of the facility's operation with respect to a heart experiencing aortic valve regurgitation. FIG. 12 is a sample ultrasound diagram showing the pathological heart at a first time. Diagram 1200 shows a color box 1270 placed for color Doppler mode by the facility to identify regions and directions of blood flow in the area of the aortic valve 1230. Blue region 1231 shows blood beginning to flow from the left ventricle 1233 to the aorta 1232 through the aortic valve.

Figure 13:
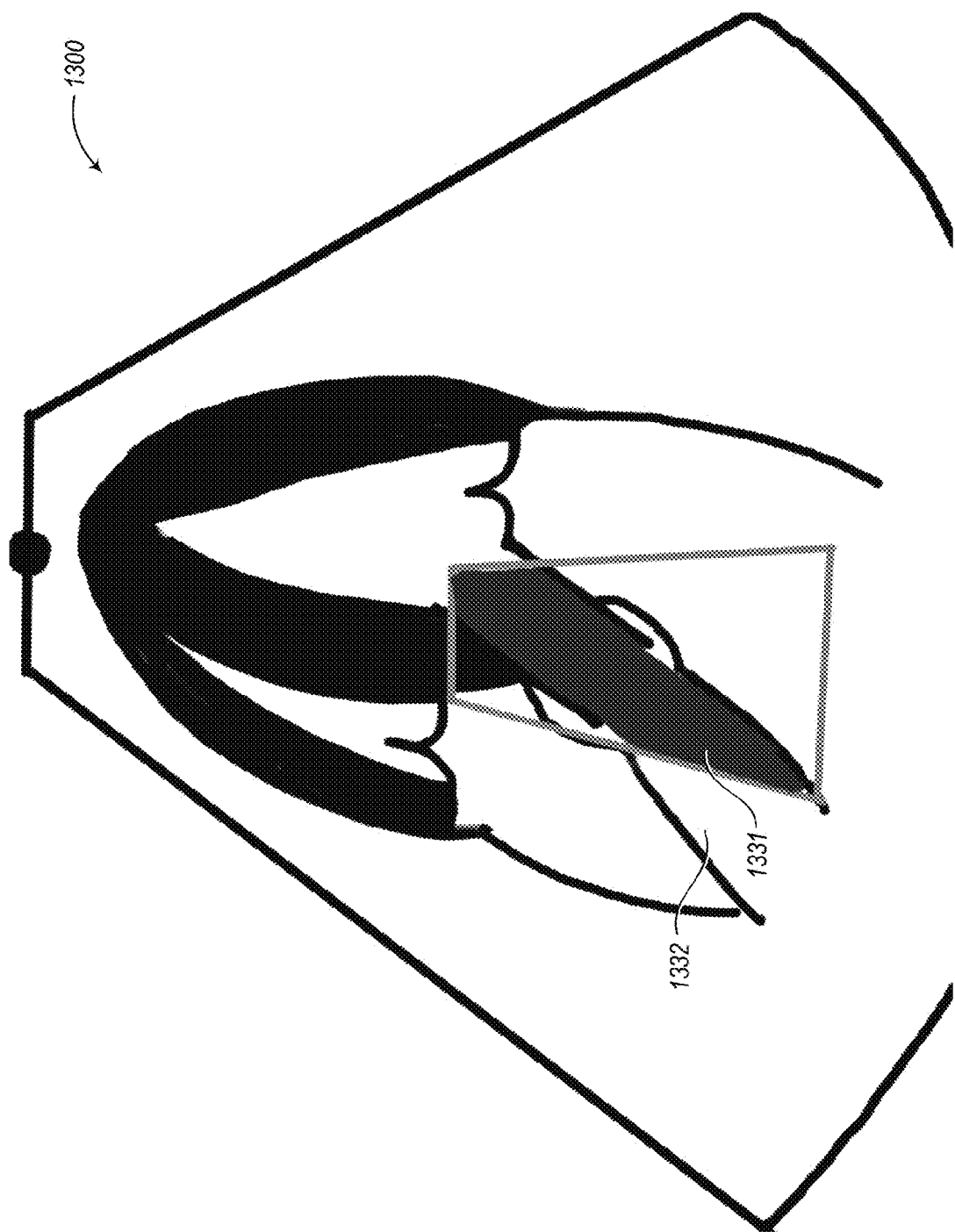
FIG. 13 is a sample ultrasound diagram showing the pathological heart at a second time.

FIG. 13 is a sample ultrasound diagram showing the pathological heart at a second time. Diagram 1300 shows shifting of the blue region 1331 further into the aorta 1332.

Figure 14:
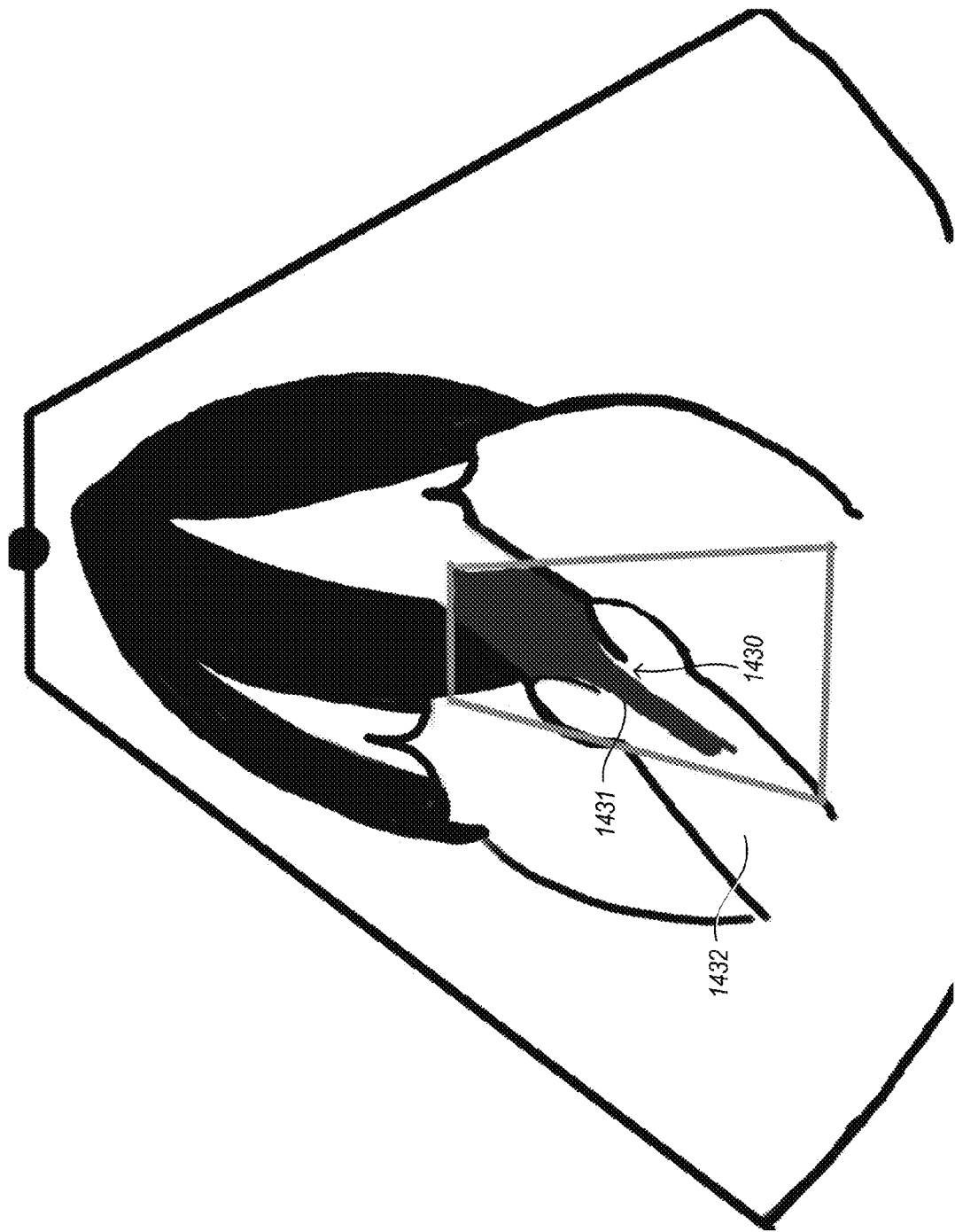
FIG. 14 is a sample ultrasound diagram showing the pathological heart at a third time.

FIG. 14 is a sample ultrasound diagram showing the pathological heart at a third time. At the third time, the aortic valve 1430 has begun to close, slackening of the flow of blood into the aorta 1432 represented by blue region 1431.

Figure 15:
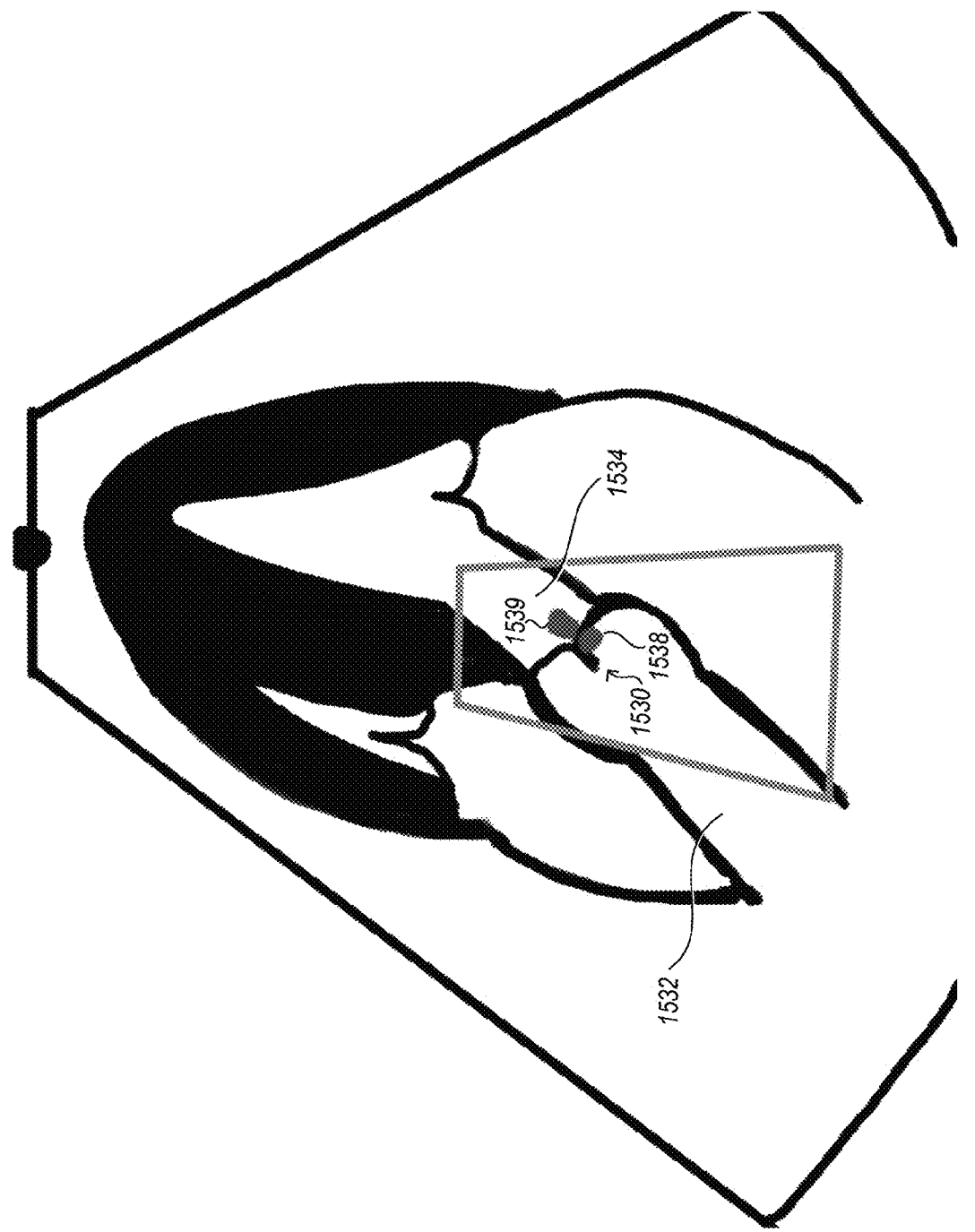
FIG. 15 is a sample ultrasound diagram showing the pathological heart at a fourth time.

FIG. 15 is a sample ultrasound diagram showing the pathological heart at a fourth time. At the fourth time, the aortic valve 1530 is in fully closed position. Despite this, blood is beginning to flow from the aorta 1532 into the left ventricular outflow tract 1534, as a result of the aortic valve's inability to fully seal when closed. This is shown by the red regurgitation jet made up of flow convergence region 1538 and jet body 1539.

Figure 16:
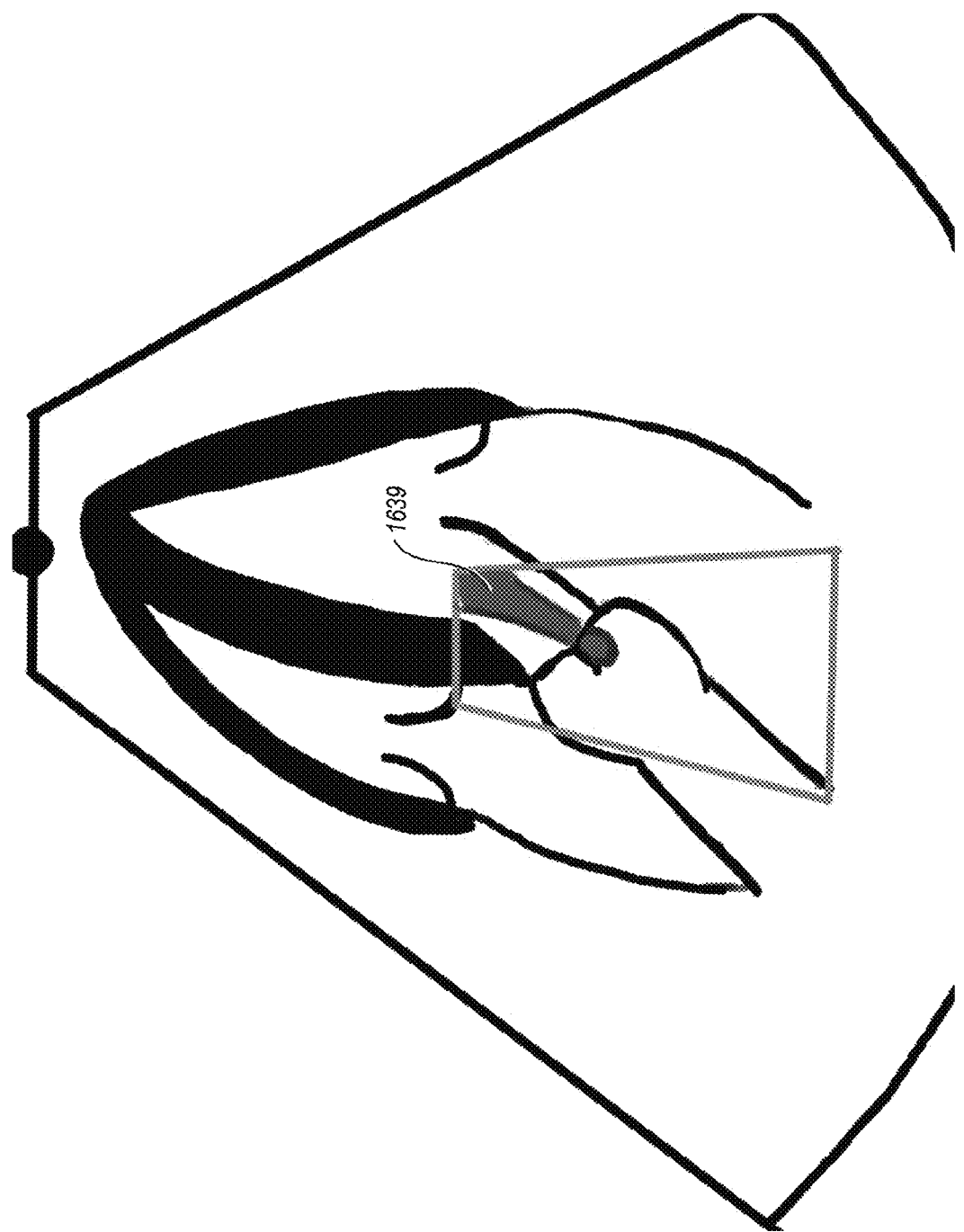
FIG. 16 is a sample ultrasound diagram showing the pathological heart at a fifth time.

FIG. 16 is a sample ultrasound diagram showing the pathological heart at a fifth time. At the fifth time, the regurgitation flow is more substantial, and jet body 1639 has grown area when compared to jet body 1539 shown in FIG. 15. In some embodiments, in order to gauge the severity of the regurgitation, the facility places measurement location controls relative to the regurgitation jet. In some embodiments, the facility determines whether the Doppler plane is passing through the entire jet in a way that is mostly parallel to the direction of the flow. In some embodiments, the facility does so by determining whether both the convergence region and body of the jet are visualized clearly in the ultrasound image. If so, there is little deviation between the flow direction and the velocity measurement direction in the Z dimension (i.e., the dimension in which probe fanning is performed), and the flow velocity in the flow measurement direction more closely resembles the flow velocity in the flow direction and can be used directly as a proxy therefor with reasonable accuracy, or can be adjusted using trigonometric calculation as described above.

The facility can be applied in a wide variety of ultrasound imaging scenarios, using a wide variety of views of each of a wide variety of organs or other anatomical areas or features. A handful of non-exclusive examples include the following.

Organ: Heart
View: PSAX (Parasternal Short Axis) base of the heart
Doppler type: CW
Pathology to be ruled out: Regurgitation
Structure: Tricuspid valve
Use case: Detect Tricuspid Regurgitation (TR) using Color Doppler to better align the CW line to the TR flow
Process: Align the CW line in parallel to the regurgitation jet.

Organ: Heart
View: PSAX (Parasternal Short Axis) base of the heart
Doppler type: PW
Use case: measure acceleration time; RVOT VTI (Velocity Time Integral), QP:QS (P—Pulmonary and S—Systemic, Q—flow rate)
Structure: Pulmonary valve (PV)
Process: Automatically place the PW line across the PV and the gate just below the PV leaflets (at the RVOT-Right Ventricular Outflow Tract).

Organ: Heart
View: PSAX (Parasternal Short Axis) base of the heart
Doppler type: CW
Pathology to be ruled out: Regurgitation/Stenosis
Structure: Pulmonary valve (PV)
Process: Automatically place the CW line across the PV and CW focal point just below the PV to measure PV velocity.

Organ: Heart
View: A4C (Apical 4-Chamber)
Doppler type: PW/CW
What will be assessed: Regurgitation/Stenosis (CW) Diastolic function (PW)
Structure: Mitral valve (MV)
Process: PW: Automatically place the PW line across the MV and the PW gate at the tips of MV leaflets to assess MV inflow. CW: (Regurgitation: atrial side, Stenosis: ventricle side)+Color to better position the focal point.

Organ: Heart
View: A4C (Apical 4-Chamber)
Doppler type: CW
Pathology to be ruled out: CW: Regurgitation
Structure: tricuspid valve (TV)
Process: Detect Tricuspid Regurgitation (TR) using Color Doppler to better align the CW line to the TR flow. Automatically place the CW line across the TV and the CW focal point just at the TV leaflet to measure PV velocity. +Color to better position the focal point.

Organ: Heart
View: A5C (Apical 5-Chamber) and A3C (Apical 3-Chamber)
Doppler type: PW
Purpose: assessment of LVOT flow/VTI, Obstruction, stroke volume, used in aortic valve area
Structure: Aortic Valve (AV)
Process: Automatically place the PW line at the hinge points of the aortic valve and PW gate just below AV leaflets (at the LVOT—Left Ventricular Outflow Tract), ~5 mm below the AV.

Organ: Heart
View: A5C (Apical 5-Chamber) and A3C (Apical 3-Chamber)
Doppler type: CW
Purpose: assessment of AV flow
Structure: Aortic Valve (AV)
Process: Automatically place the CW line across the aortic valve and CW focal point just at the AV leaflet. Use color aliasing to predict highest velocity flow. Use color direction to determine Regurgitation vs Stenosis.

Organ: Heart
View: Subcostal short axis view
Doppler type: PW
Structure: Hepatic Veins
Purpose: To assess hepatic vein blood flow velocity and flow pattern
Automatically detect Hepatic Veins
Color Doppler at a low velocity scale is used to identify the HV
Process: Automatically align the PW line through Hepatic Veins and automatically place the PW gate in the center of Hepatic Veins 1 to 2 cm proximal to its junction to the IVC.

Organ: Heart
View: Inferior Vena Cava (IVC)
Doppler type: PW
Structure: IVC
Purpose: To assess IVC blood flow velocity and flow pattern
Automatically detect IVC
Color Doppler at a low velocity scale is used to identify the IVC
Process: Automatically align the PW line through IVC and automatically place the PW gate in the center of IVC.

Organ: Heart
View: Subcostal short axis view
Doppler type: PW
Structure: Hepatic Veins/Abdominal Aorta
Purpose: To assess hepatic vein blood flow velocity and flow pattern, to assess Abdominal Aorta for holodiastolic reversal of flow associated with significant Aortic Regurgitation Automatically detect Hepatic Veins/Proximal Descending and Abdominal Aorta Color Doppler at normal velocity scale Process: Automatically align the PW line through the Abdominal Aorta s and automatically place the PW gate in the center of the Abdominal Aorta.

Organ: Heart

View: Suprasternal Notch

Doppler Type: PW/CW

Structure: Aortic Arch (PW)/Descending Aorta (CW)

Purpose: Regurgitation of AV or obstruction of AO

Automatically detect of Aortic Arch

Process: Color Doppler at standard velocity scale to detect aliasing (presence of higher velocities). >2 m/sec. Automatically align the PW line through Descending Aorta, place sample gate 1 cm distal to origin of left subclavian artery. PW at proximal descending aorta can be used to assess for holo-diastolic flow reversal associated with Severe Aortic Regurgitation. Automatically align the CW line through the descending aorta with focal point at color aliasing. Indicate Obstruction (co-arct—common with bicuspid AV valves).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
an ultrasound transducer; and
a computing device configured to directly receive ultrasound data sensed by the ultrasound transducer from a person, the received ultrasound data comprising a sequence of ultrasound images, the computing device comprising:
 a processor configured to perform a method, the method comprising:
  receiving a first ultrasound image from the ultrasound transducer;
  receiving user input selecting an anatomical structure appearing in the first ultrasound image;
  performing localization based on segmentation or key point detection of the first ultrasound image performed by:
   applying a convolutional neural network to aliasing patterns in the first ultrasound image that are associated with blood flow through the person to obtain a probability map signifying a spatial location of the aliasing patterns in the first ultrasound image and the direction of the blood flow; and
   determining a location of the selected anatomical structure in the first ultrasound image based on the probability map;
  automatically performing a first placement of measurement location controls relative to the determined location of the selected anatomical structure;
  causing the ultrasound transducer to implement one or more first Doppler ultrasound modes using the determined first measurement location control placement;
  receiving one or more second ultrasound images from the ultrasound transducer using the one or more first Doppler ultrasound modes;
  determining a flow location and flow direction based on the one or more second ultrasound images;
  automatically performing a second placement of measurement location controls relative to the determined flow location;
  causing the ultrasound transducer to implement one or more second Doppler ultrasound modes using the second measurement location control placement; and
  receiving results in response to causing the ultrasound transducer to implement the one or more second Doppler ultrasound modes.

2. The system of claim 1 wherein the one or more first Doppler ultrasound modes comprise color Doppler mode, and wherein the one or more second Doppler ultrasound modes comprise pulsed wave Doppler mode.

3. The system of claim 2 wherein the first placement of measurement location controls places a color box,
and wherein the second placement of measurement location controls places a Doppler line and a gate.

4. The system of claim 1 wherein the one or more first Doppler ultrasound modes comprise color Doppler mode, and wherein the one or more second Doppler ultrasound modes comprise continuous wave Doppler mode.

5. The system of claim 4 wherein the first placement of measurement location controls places a color box,
and wherein the second placement of measurement location controls places a Doppler line.

6. The system of claim 1 wherein the received results comprise one or more third ultrasound images received from the ultrasound transducer while the ultrasound transducer is implementing one or more third Doppler ultrasound modes, the one or more third ultrasound images showing flow location and direction relative to anatomical structures appearing in the one or more third ultrasound images.

7. The system of claim 1 wherein the received results comprise a flow velocity determined in the implementation of the one or more second Doppler ultrasound modes.

8. An ultrasound machine, comprising:
an ultrasound transducer; and
a computing device configured to directly receive ultrasound data sensed by the ultrasound transducer from a person, the received ultrasound data comprising a sequence of ultrasound images, the computing device comprising:
 a processor configured to perform a method, the method comprising:
  receiving a first ultrasound image from the ultrasound transducer;
  receiving user input selecting an anatomical structure appearing in the first ultrasound image;
  performing localization based on aliasing patterns in the first ultrasound image that are associated with aberrant blood flow through the person to determine the location of the selected anatomical structure in the first ultrasound image;

automatically performing a first placement of measurement location controls relative to the determined location of the selected anatomical structure;

causing the ultrasound transducer to implement one or more first Doppler ultrasound modes using the determined first measurement location control placement;

receiving one or more second ultrasound images from the ultrasound transducer using the one or more first Doppler ultrasound modes;

determining a flow location and flow direction based on the one or more second ultrasound images;

automatically performing a second placement of measurement location controls relative to the determined flow location;

causing the ultrasound transducer to implement one or more second Doppler ultrasound modes using the second measurement location control placement; and receiving results in response to causing the ultrasound transducer to implement the one or more second Doppler ultrasound modes.

9. The ultrasound machine of claim 8 wherein the one or more first Doppler ultrasound modes comprise color Doppler mode, and wherein the one or more second Doppler ultrasound modes comprise pulsed wave Doppler mode.

10. The ultrasound machine of claim 9 wherein the first placement of measurement location controls places a color box, and wherein the second placement of measurement location controls places a Doppler line and a gate.

11. The ultrasound machine of claim 8 wherein the one or more first Doppler ultrasound modes comprise color Doppler mode, and wherein the one or more second Doppler ultrasound modes comprise continuous wave Doppler mode.

12. The ultrasound machine of claim 11 wherein the first placement of measurement location controls places a color box, and wherein the second placement of measurement location controls places a Doppler line.

13. The ultrasound machine of claim 8 wherein the received results comprise one or more third ultrasound images received from the ultrasound transducer while the ultrasound transducer is implementing one or more third Doppler ultrasound modes, the one or more third ultrasound images showing flow location and direction relative to anatomical structures appearing in the one or more third ultrasound images.

14. The ultrasound machine of claim 8 wherein the received results comprise a flow velocity determined in the implementation of the one or more second Doppler ultrasound modes.

* * * * *